United States Patent
Rosenblatt et al.

(10) Patent No.: US 6,942,635 B2
(45) Date of Patent: Sep. 13, 2005

(54) BLOOD TREATMENT CATHETER AND METHOD

(75) Inventors: Melvin Rosenblatt, New Rochelle, NY (US); William M. Appling, Granville, NY (US); Donald R. Geer, Queensbury, NY (US); Ted Beyer, Queensbury, NY (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 10/116,299

(22) Filed: Apr. 4, 2002

(65) Prior Publication Data

US 2003/0191425 A1 Oct. 9, 2003

(51) Int. Cl.[7] .......................... A61M 37/00; A61M 3/00; A61M 3/02; A61M 25/00; A61M 31/00
(52) U.S. Cl. .................. 604/6.13; 604/5.01; 604/43; 604/264; 604/523; 604/39; 604/508
(58) Field of Search ............... 604/39, 4.01, 5.01–5.04, 604/6.16, 19, 28, 43, 500, 507, 508, 93.01, 94.01–94.02, 264, 523, 534, 537; 138/115–117, 111; 210/645–46; 600/581

(56) References Cited

U.S. PATENT DOCUMENTS

| | | | | |
|---|---|---|---|---|
| 4,134,402 A | * | 1/1979 | Mahurkar | 604/44 |
| 5,053,004 A | * | 10/1991 | Markel et al. | 604/43 |
| 5,053,023 A | * | 10/1991 | Martin | 604/523 |
| 5,360,397 A | * | 11/1994 | Pinchuk | 604/27 |
| 5,718,692 A | | 2/1998 | Schon et al. | |
| 5,947,953 A | * | 9/1999 | Ash et al. | 604/508 |
| 5,961,485 A | * | 10/1999 | Martin | 604/43 |
| 6,001,079 A | | 12/1999 | Pourchez | |
| 6,461,321 B1 | * | 10/2002 | Quinn | 604/43 |
| 6,533,763 B1 | * | 3/2003 | Schneiter | 604/264 |
| 6,540,714 B1 | * | 4/2003 | Quinn | 604/43 |
| 6,814,718 B2 | | 11/2004 | McGuckin, Jr. et al. | 604/264 |
| 2002/0107506 A1 | * | 8/2002 | McGuckin et al. | 604/523 |

* cited by examiner

*Primary Examiner*—Patricia Bianco
(74) *Attorney, Agent, or Firm*—Reed Smith LLP

(57) ABSTRACT

Disclosed are various embodiments of a hemo-dialysis catheter in which the aspirating port at the end of the aspirating tube is distal of the infusion port or ports at the end of the infusion lumen. The infusion port or ports are arranged circumferentially so that the infused filtered blood is a substantially 360° jet of fluid with a substantial radial component. This jet of fluid serves to abrade the occlusive material that is composed of fibrin and other components that grows down along the outer wall of the catheter that would otherwise tend to block off the ports. Stopping occlusion growth at the zone of the infusion ports prevents further growth distally to the aspirating port and protects the aspirating port from being blocked by the growth of occlusion.

10 Claims, 16 Drawing Sheets

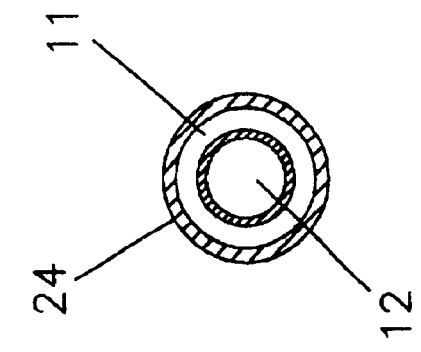
Fig.12D
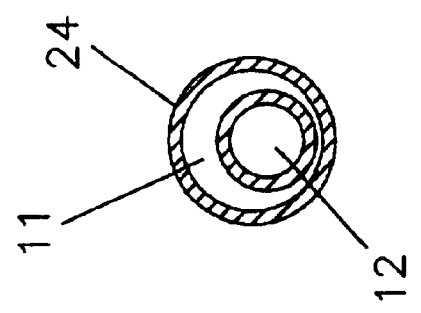
Fig.12C
Fig. 12
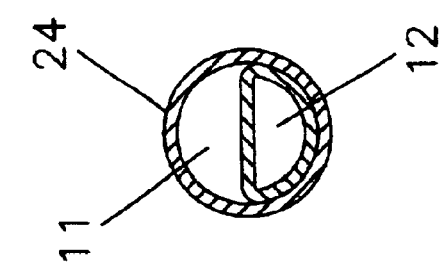
Fig.12B
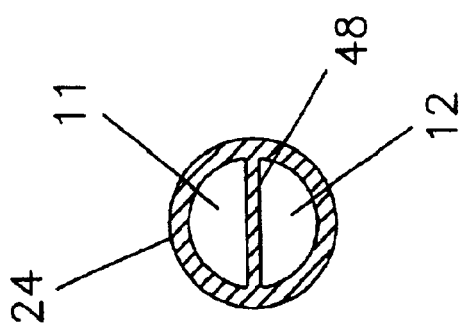
Fig.12A

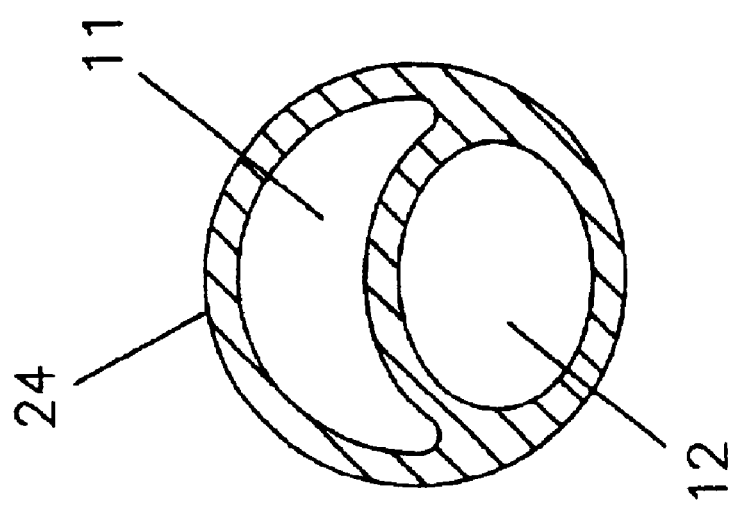

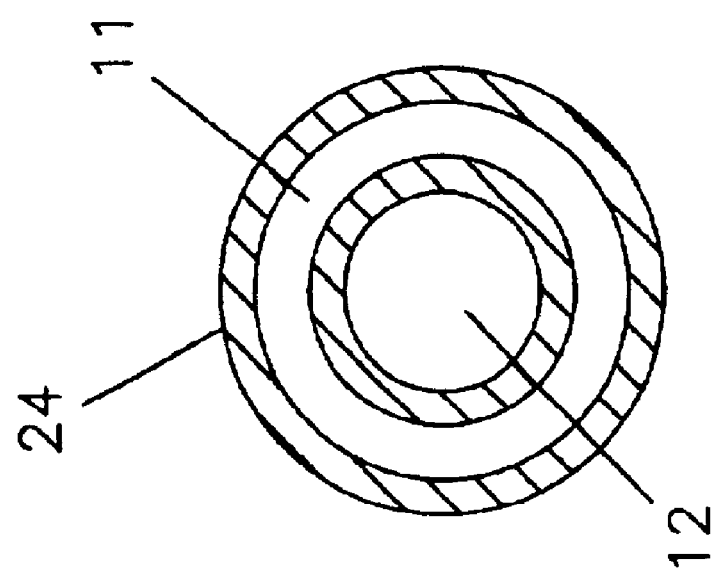

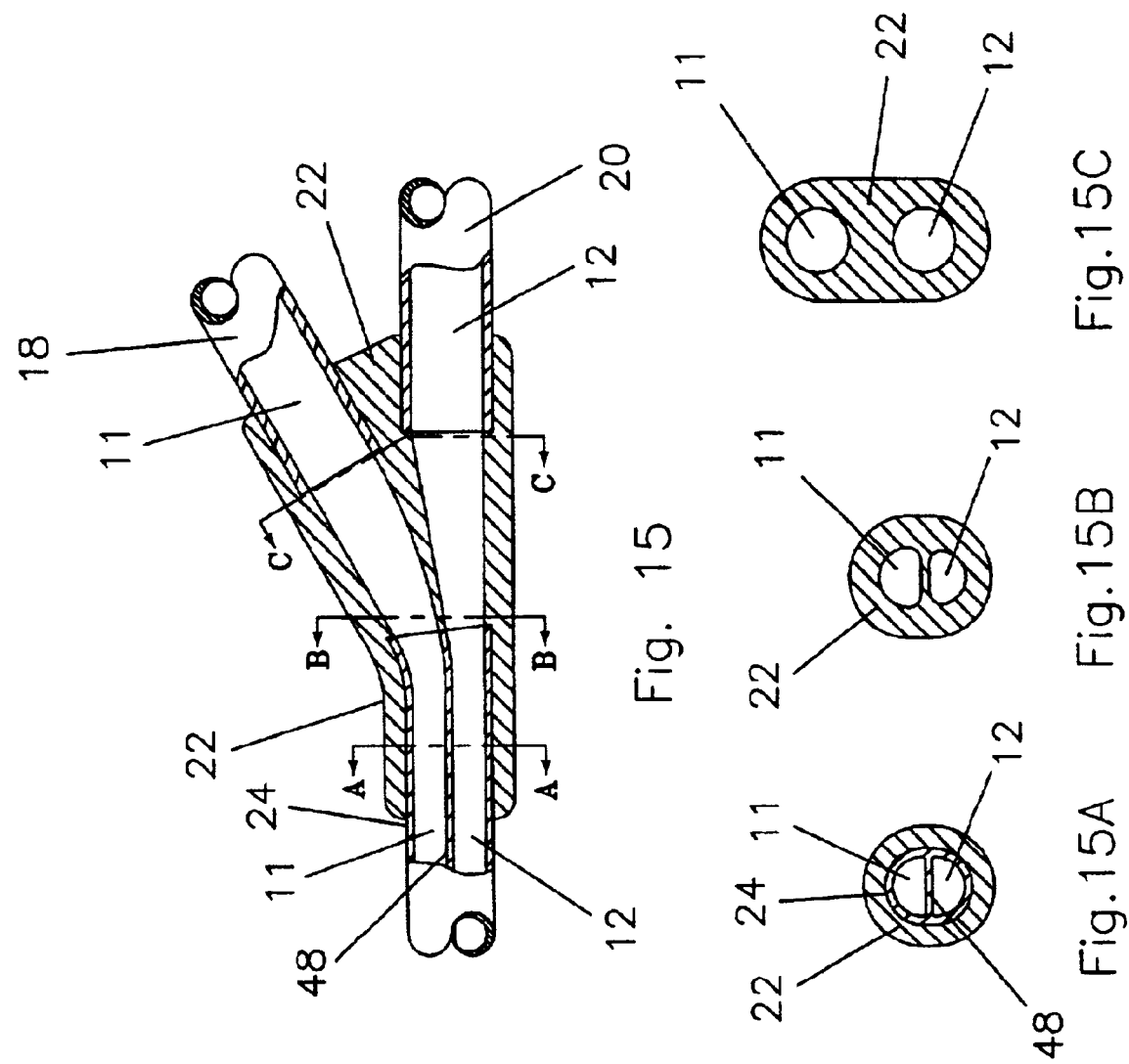

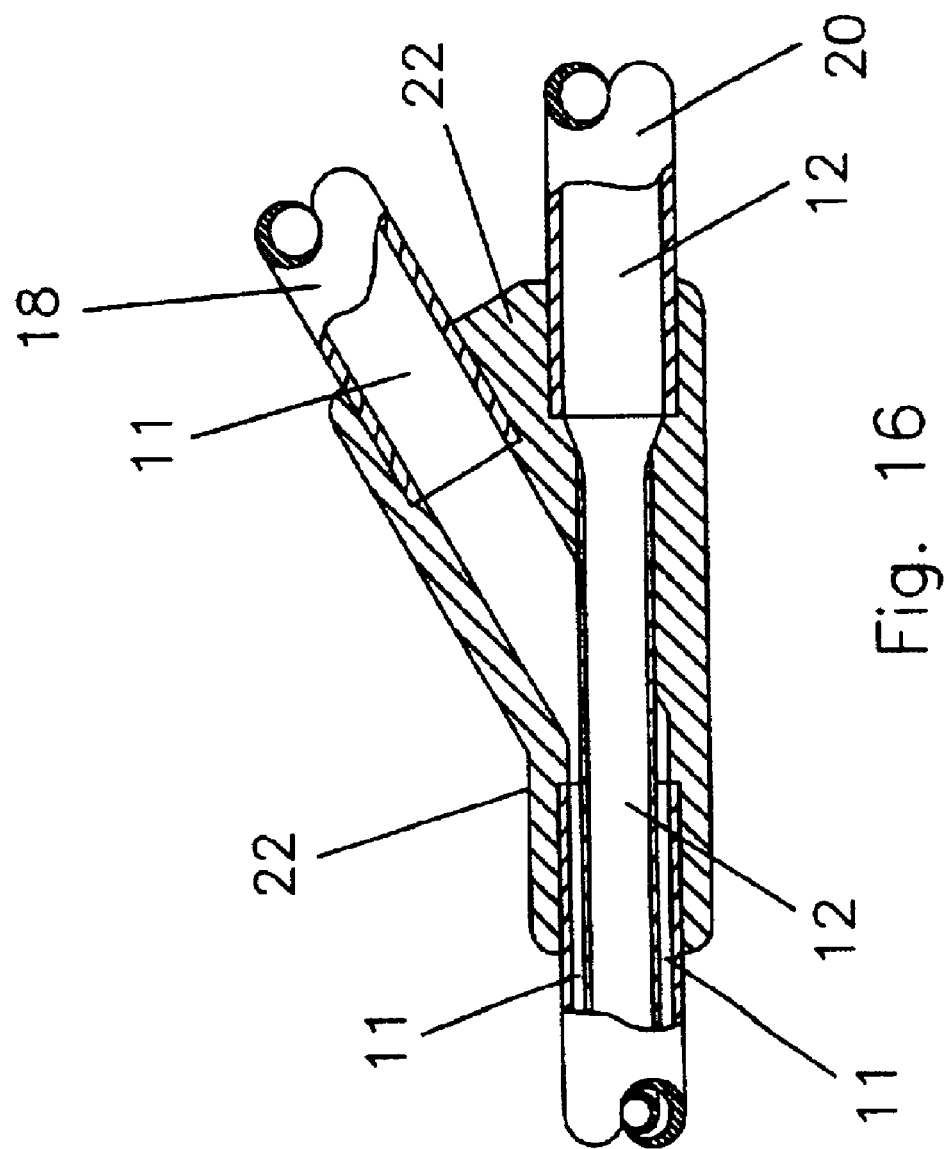

BLOOD TREATMENT CATHETER AND METHOD

BACKGROUND OF THE INVENTION

This invention relates in general to blood treatment catheters and more particularly to a design for use in hemo-dialysis in which the occlusion of the distal ports due to fibrin buildup is substantially eliminated.

Hemo-dialysis is the process of mass transfer, in which certain chemical substances, accumulated in the blood because of kidney failure, are transferred from the blood across a semi permeable dialysis membrane to a balanced salt solution. The efficiency of a hemo-dialysis procedure depends on the amount of blood brought into contact with the dialysis membrane. A flow of 250 milliliters of blood per minute under a pressure gradient of 100 millimeters of mercury is considered a minimum requirement for adequate dialysis. Over the past several years, flow rate between 350 milliliters per minute and 400 milliliters per minute have become common.

At the place where the catheter is inserted into the patient, the body reacts by creating a sheath of material that includes fibrin and other materials that grow down the outer wall of the catheter from the point of insertion in the vein. This material is referred to herein as occlusive material. This occlusive material when it grows down to the site of ports, and most particularly the aspirating port, tends to block the ports rendering the catheter essentially useless.

Accordingly, it is the primary object of this invention to create a catheter design that substantially eliminates or reduces the build up of occlusion at the infusion and aspirating ports.

BRIEF DESCRIPTION

In brief, the catheter disclosed has both aspirating and infusion lumens. At a distal zone, the tube carrying the aspirating lumen extends distally of the end of the tube defining the infusion lumen. At its distal end, the infusion lumen is substantially annular around the aspirating tube and has infusion ports that provide emission of fluid over substantially 360° as a jet like emission having a significant radial component. A nose of a built up zone on the outside of the aspirating tube, immediately adjacent to and distal of the exit port from the infusion lumen, provides a wall for the exit port to assure that the jet of fluid exits in a substantially radial direction.

This jet of infusion fluid abrades the occlusion that tends to grow down these catheters from the point of insertion into the patient. Thus the 360° infusion jet prevents such occlusive material not only from clogging the infusion port but also prevents further distal growth along the aspirating tube. This means that occlusion of the end of the aspirating tube by occluding material is avoided.

Definitions

The term occlusion or occlusive material refers to the well known coating that builds up on the exterior of these catheters. It starts at approximately the point where the catheter is inserted through the vein and builds down along the outside surface of the catheter. This occlusion build up is believed to be composed of a number of materials such as fibrin, and/or muscle cells and/or blood clot.

This invention is addressed to a technique of preventing the occlusion build up from extending down over the end of the aspirating port or ports and causing the aspirating ports to block.

Infusion and Aspirating Port and Ports

The preferred embodiments, shown in FIGS. 3 through 6 contain a plurality of infusion exit ports. As discussed in connection with FIG. 7, a design can be provided in which there is a single circumferential exit port. An essential feature is that there is a substantial 360° jet having a substantial radial component which serves to abrade and clear away occlusion that grows down the outer wall of the catheter. The aspirating port, though shown as a single end port can be a plurality of circumferential ports and the term "port" is used to include the multiple port arrangement.

Accordingly, it should be understood herein that the terms "port" or "ports" or "port arrangement" in the specification and claims are used to include a single port and/or a set of ports, such as the ports 26a of FIG. 3 and the ports 26b of FIG. 5.

BRIEF DESCRIPTION OF THE FIGURES

In FIG. 1, the catheter is inserted into the patient at point A and into the vein at point B.

FIG. 3 is a larger scale elevation view of the zone around the distal infusion port of an embodiment of the FIG. 2 catheter having a plurality of angled infusion ports 26a.

FIG. 9 illustrates the umbrella-like shape of the infusion 40 that results from the combined effect of the radial jet of filtered blood from the infusion ports 26b and the downward flow of the patient's blood.

FIGS. 12A, 12B, 12C and 12D are cross-sectional views along the planes A—A, B—B, C—C and D—D respectively, of FIG. 11 showing a presently preferred embodiment of this invention. These cross-sectional FIGS. show the transition from the semi-circular lumens 11, 12 that exist along about eighty percent of the length of the catheter to the coaxial lumen arrangement immediately proximal of the infusion port 26.

FIG. 13 is a cross-sectional view along the plane A—A of FIG. 11 illustrating a further embodiment of this invention showing two shaped lumens 11,12 that exist over at least eighty percent of the length of the catheter. FIGS. 12C and 12D illustrate the transition of the FIG. 13 embodiment to the coaxial lumen arrangement immediately proximal of the infusion port 26.

FIG. 14 is a cross-sectional view along the plane A—A of FIG. 11 illustrating another embodiment of this invention in which the two lumens 11, 12 are coaxial along the entire length from the juncture 22 to the infusion port 26. In the FIG. 14 embodiment, the support web shown at FIG. 8 would be employed.

FIG. 15 is a longitudinal sectional view through the connector 22 for the FIGS. 12A–12D embodiment having the substantially semicircular lumens 11 and 12. FIGS. 15A, 15B and 15C are cross-sectional views along the planes A—A; B—B and C—C, respectively, of FIG. 15.

FIG. 16 is a longitudinal sectional view of the connector for the FIG. 14 embodiment in which the lumens 11, 12 are concentric from juncture 22 to infusion port 26.

DESCRIPTION OF THE PREFERRED EMBODIMENTS

Figure 1:
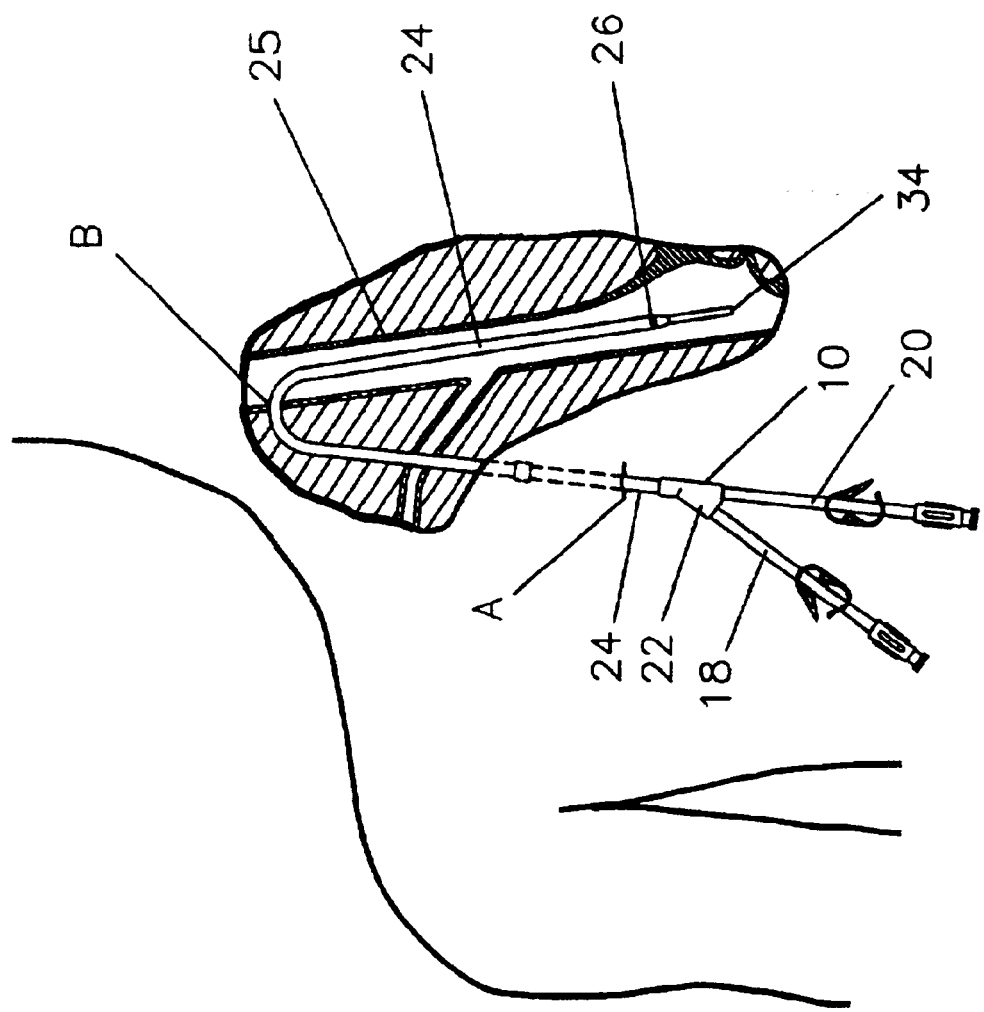
FIG. 1 is a schematic illustration of the positioning of the hemo-dialysis catheter of this invention through the jugular vein.

The catheter 10 of this invention has an infusion lumen 11 and an aspirating lumen 12. The distal end 16 of the aspirating lumen extends distally beyond the distal end 14 of the infusion lumen 11.

Figure 2:
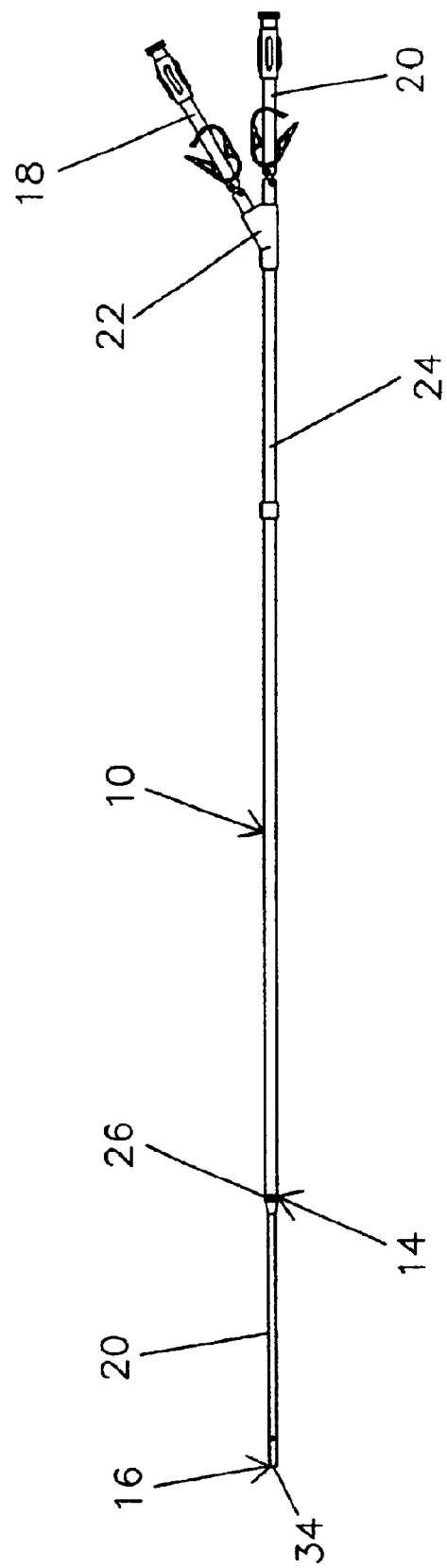
FIG. 2 is an elevation view of a catheter of this invention showing the infusion tube 18 and aspirating tube 20 combined at juncture 22 to form the main portion 24 of the catheter. Infusion ports 26 are at the distal end of the infusion lumen. Aspirating port 34 is at the distal end of the aspirating tube 20.
Figure 10:
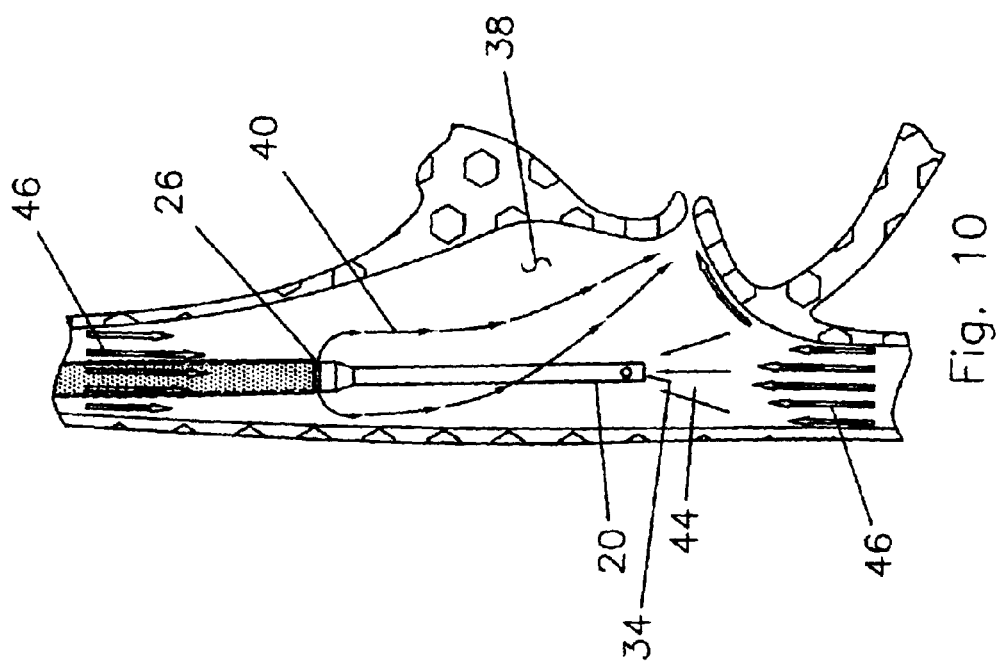
FIG. 10 is a schematic illustration of blood flow into and from the catheter of this invention at the right atrium.

More particularly with respect to FIGS. 1 and 2, a standard infusion tube 18 and aspirating tube 20 are combined at a juncture 22 to provide a single tube 24 distal of the juncture 22. The tube 24 contains infusion and aspirating lumens. The tube 24 is inserted into a patient at point A and passed into the jugular vein 25 at point B to be positioned at a desired location; often in the right atrium 38 as shown in FIG. 10.

Figure 3:
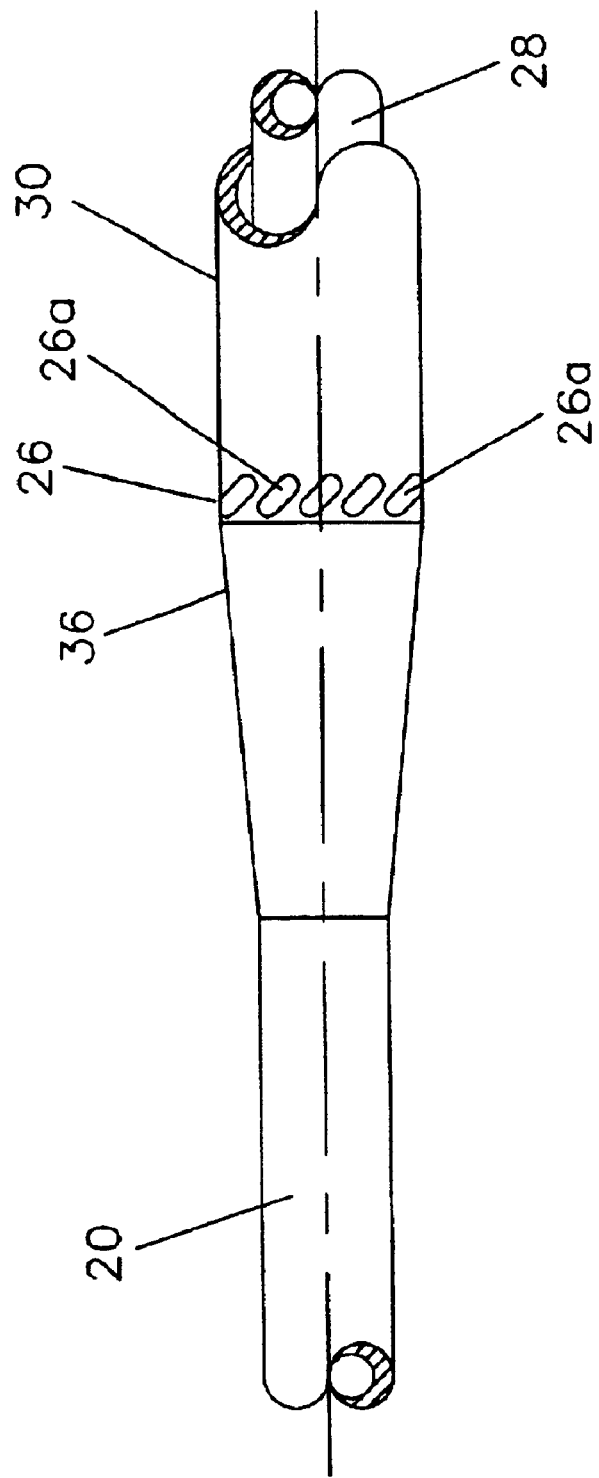
Figure 4:
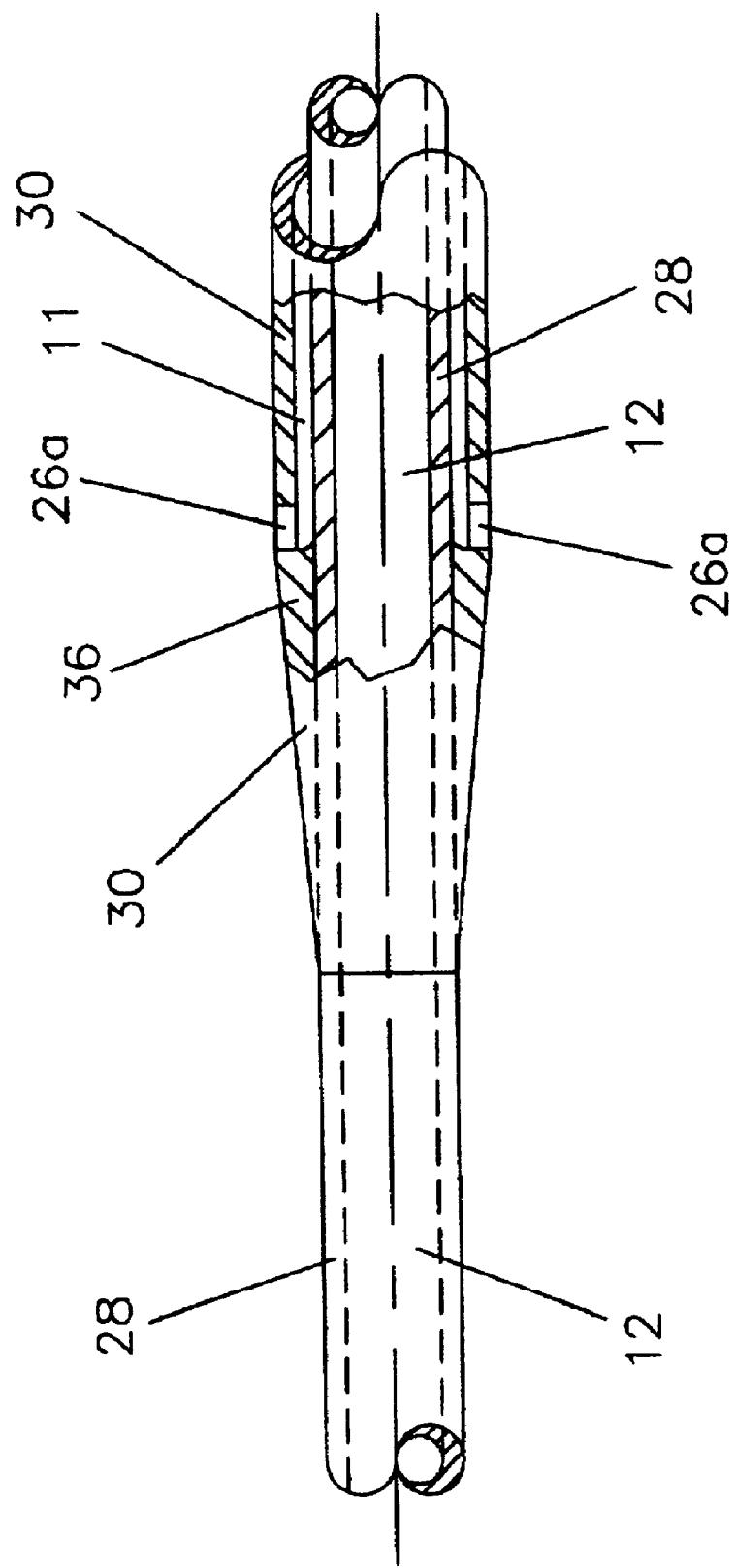
FIG. 4 is a partial longitudinal sectional view through the FIG. 3 catheter portion.

FIGS. 3 and 4 illustrate a presently preferred embodiment of this invention in which the infusion port set 26 is constituted by ten ports 26a each having a major axis at an angle of approximately 45° to a circumferential line through the ports 26a. In this embodiment, each of the ports is approximately 50 mils (0.050 inches) by 20 mils (0.020 inches). These ports 26a are at the distal end of the infusion lumen 11.

As can best be seen in FIG. 4, the infusion lumen 11 is a circumferential lumen around the aspirating lumen 12 in the zone that is immediately proximal of the infusion exit ports 26a. An inner wall 28 defines the aspirating lumen 12. The infusion lumen 11 is defined by the inner wall 28 and the outer wall 30. Each port 26a is a port in the outer wall 30. The outer wall 30 merges into the inner wall 28 at the zone 36. This provides a terminal wall for the infusion lumen 11 and assures that the infusing filtered blood is ejected through the set of ports 26a in a substantially radial direction.

Figure 5:
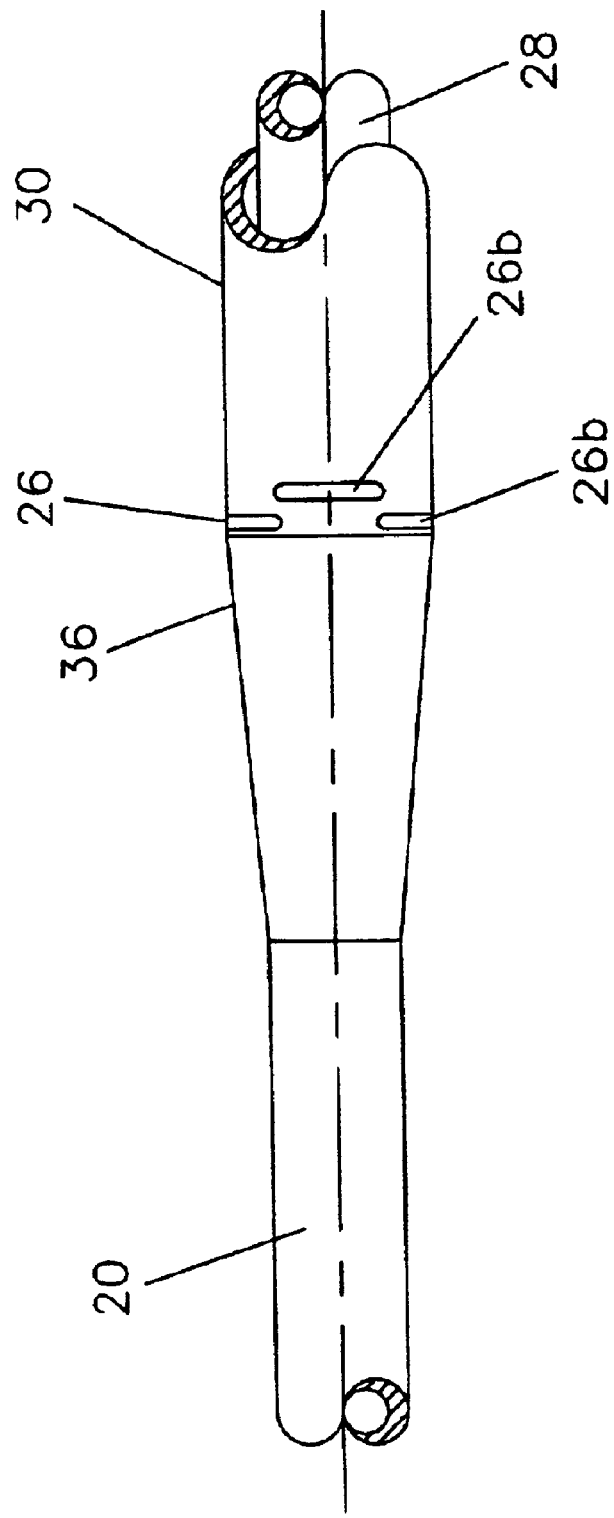
FIG. 5 is a larger scale elevation view of the zone around the distal infusion port of a second embodiment of the FIG. 2 catheter showing a plurality of arcuate circumferential ports 26b.
Figure 6:
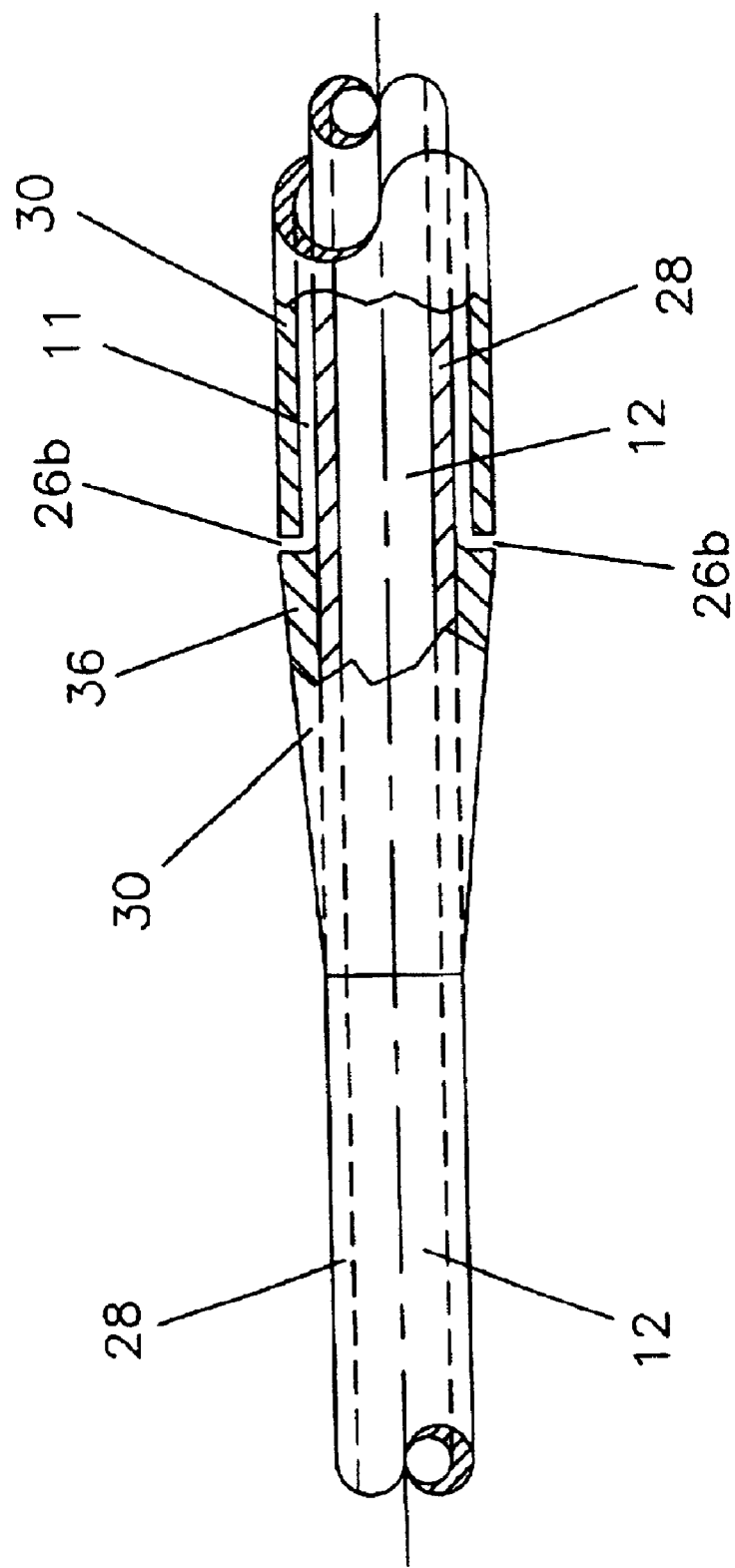
FIG. 6 is a partial longitudinal sectional view along the FIG. 5 catheter portion.

FIGS. 5 and 6 illustrate a modified version of the FIGS. 3 and 4 embodiment. The difference in this embodiment is that the distal infusion exit port 26 is composed of a plurality of circumferential ports 26b. Each of these circumferential ports 26b is approximately 20 mils (0.020 inches) wide.

In one embodiment, six such openings are involved. Each opening covers an arc of about 70°. The two subsets of three circumferentially aligned openings are axially spaced from one another by 45 mils (0.045 inches) centerline to centerline. The FIGS. 5 and 6 embodiment is the same as that of FIGS. 3 and 4 including the employment of the buildup section or nose at the zone 36 that serves to provide an end wall for the infusion lumen 11 and that provides an exit passageway that assures the infusing blood will exit in a substantially radial direction.

Figure 7:
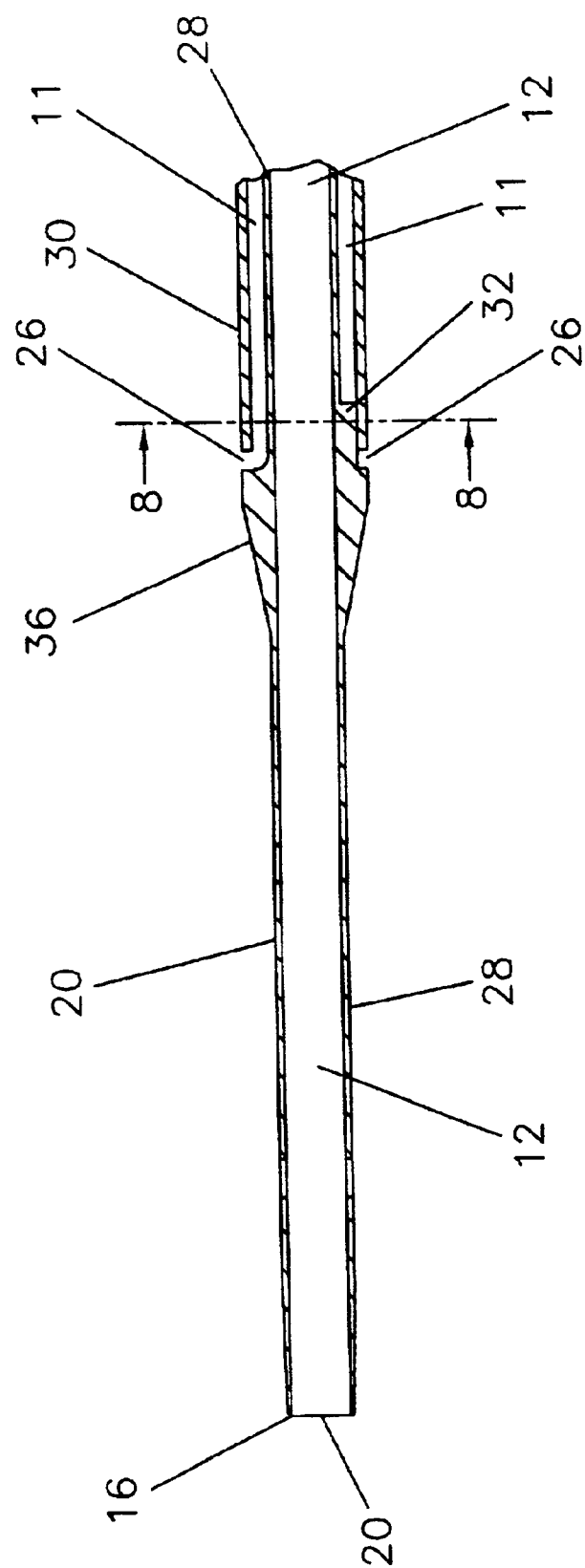
FIG. 7 is a longitudinal sectional view of a further embodiment of the FIG. 2 catheter in which the infusion port 26 is substantially a 360° circumferential port.
Figure 8:
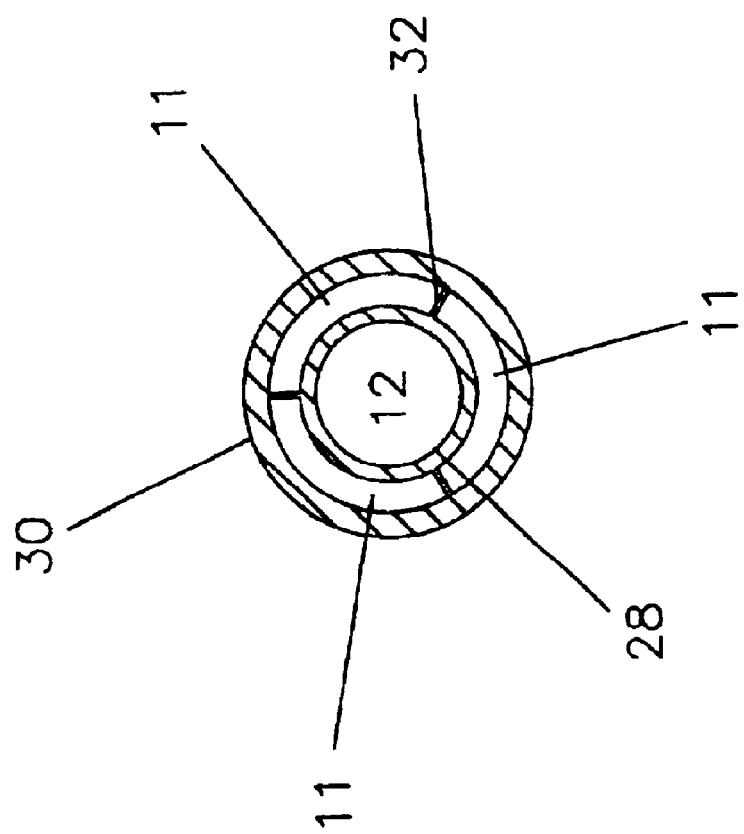
FIG. 8 is a cross-sectional view along the plane 8—8 of FIG. 7 showing a three chamber section of the circumferential infusion lumen 11 immediately adjacent to the infusion port 26.

FIGS. 7 and 8 illustrate a third embodiment of this invention in which the exit port 26 is a 360° circumferential port.

In order to assure that the 360° port is maintained open and to prevent the wall 30 from collapsing onto the wall 28 over a portion of the exit port arrangement, a web design, shown in FIG. 8, is employed at the exit port 26. This web design involves three thin webs 32 which extend from the zone 36 proximally for about three millimeters in the embodiment shown.

The web 32 supports are not required in the design shown in FIGS. 3 through 6. In those designs, the outer wall 30 extends past the ports 26a or 26b to merge into the wall 28 of the aspirating lumen and thus does not require extra support. However, it should be understood that the design of this invention includes an embodiment in which the FIG. 8 web extends the length of the catheter from junction 22 to infusion exit port 26. Such a design is not presently preferred because it provides a stiffer catheter than do the designs disclosed herein.

In all three of the embodiments shown in FIGS. 3 through 8, the jet of fluid provided at the infusion port 26 serves to prevent buildup of occlusion distal of those ports. It is believed that a key factor is that the occlusion is physically abraded by the jet of fluid.

Figure 9:
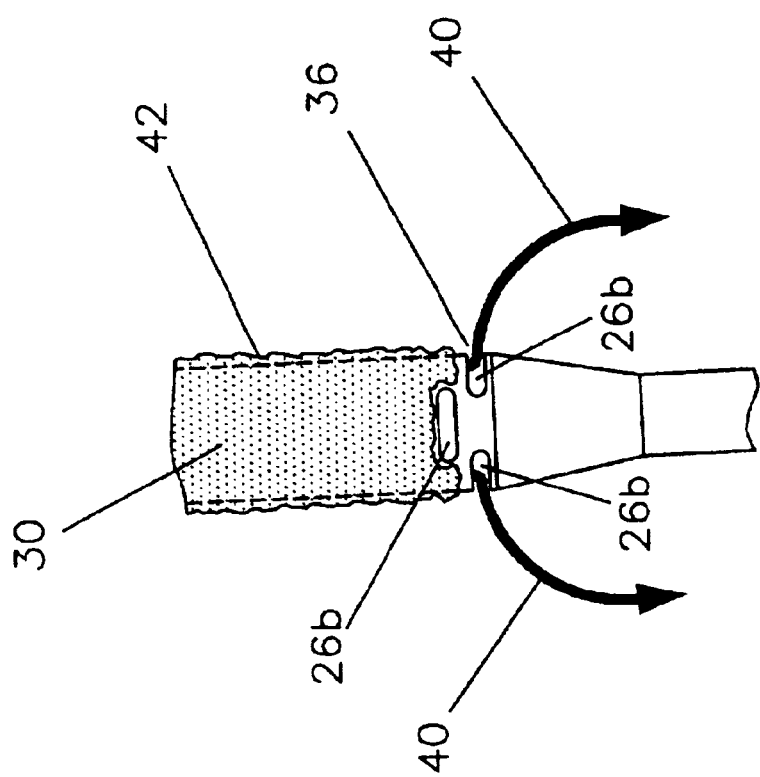
FIG. 9 is a schematic illustration of the infusion of filtered blood at the infusion ports of the infusion lumen.

As shown in highly schematic form in FIG. 9, the jet of filtered blood 40 exits from the ports 26b in a radial direction and then as it joins the flow of patient's blood, becomes more axially oriented. As shown in FIG. 9, the occlusion 42 builds up on the outer wall 30 and extends down to the ports 26b where the abrading action of the jet of filtered blood prevents further growth of the occlusion 42.

As shown schematically in FIG. 10, the hemo-dialysis catheter is frequently placed in the right atrium 38. Of the blood flow 46 coming up from the inferior vena cava into the right atrium, a portion 44 is taken in at the aspirating port 34 to be processed and filtered. The filtered blood 40 is returned as a jet from the infusion lumen. This filtered blood 40 joins the blood flow 46 coming down from the superior vena cava into the right atrium to then be circulated throughout the body.

FIG. 10 shows the catheter extending down into the right atrium. The procedure may also be such that the hemo-dialysis catheter is extending up into the right atrium. In such a situation, the infusion would be into blood from the inferior vena cava and the aspiration would be from blood from the superior vena cava. As shown in FIG. 10, the aspirating port can be in the right atrium providing it is positioned to aspirate blood flow from one of the two vena cavas and so that the infusion is sufficiently distal to provide filtered blood that merges with blood flow from the other vena cava.

A further feature of this invention can best be understood by reference to FIG. 10. A catheter design which places the aspirating port substantially distal of the infusion port 26 provides a device which reduces irritation to the walls of the right atrium 38 when disposed as shown in FIG. 10.

To avoid problems relating to the immediate recirculation through the filtering system of filtered blood, known types of catheters place the infusion port distal of the aspirating port, maintaining those two ports separated by a relatively small 1.5 to 2.5 centimeters apart. In those designs, the aspirating port is placed in the blood flow 46 in the superior or inferior vena cava. Thus vena cava blood is the source of blood to the aspirating port. The more distal infusion port that provides filtered blood is positioned at the right atrium to supply filter blood to the right ventricle.

The design of this invention has the aspirating tube extend substantially beyond the end of the infusion tube (four centimeters or more) so that the aspirating port 34 can be placed in substantial communication with the blood flow 46 from the inferior vena cava while the filtered blood 40 is supplied to the patient's heart without being partially re-circulated through the aspirating port.

The portion of the aspirating tube that extends distally of the infusion tube has a smaller diameter than the rest of the catheter. This smaller diameter together with its length makes it more flexible and less likely to irritate the walls of the right atrium 38.

Thus the design of this invention reduces immediate re-filtering of filter blood while providing the surgeon with greater choice in the positioning of the catheter while minimizing irritation.

Figure 11:
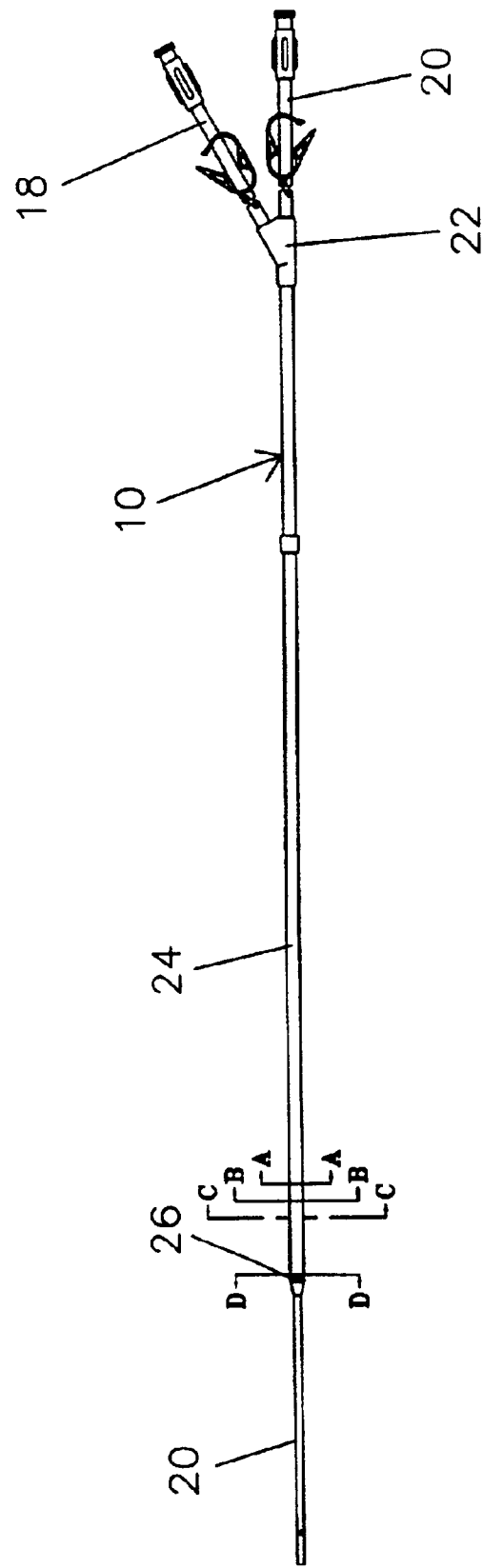
FIG. 11 is an elevation view of a generic showing of the catheter of this invention. It is used to illustrate three embodiments of this invention which differ in the configuration of the infusion and aspirating lumens over the proximal 80 to 90 percent of the catheter that is between the juncture 22 and the infusion port 26.

FIG. 11 is a sub-generic illustration of this invention. It is the basis for the disclosure of various specific arrangements of the infusion lumen 11 and aspirating lumen 12 in the tube 24 between the juncture 22 and the infusion port 26. The length of the catheter between juncture 22 and port 26 generally constitutes between 80 and 90 percent of the total catheter length.

FIG. 12A shows a preferred arrangement of the lumens 11 and 12. In this embodiment, the FIG. 12A arrangement exists through about 85% or more of the distance from the juncture 22 to the infusion port 26. This FIG. 12A arrangement involves two substantially semi-circular in cross-section lumens 11 and 12 separated by a partition 48. In order to assure the substantially 360° infusion jet at the infusion port 26, the coaxial arrangement shown in FIG. 12D is desired. To transition from the FIG. 12A arrangement to the FIG. 12D arrangement, the cross-sectional arrangement shown in FIGS. 12B and 12C are employed.

As shown in FIG. 12A, it is generally desirable that the cross-sectional area of the two lumens 11 and 12 be equal to one another. This equality is maintained as much as possible through the transition so that the cross-sectional area of the lumens 11 and 12 at the infusion exit port 26, as shown in FIG. 12D, are approximately equal. This equality of cross-sectional areas is desirable and is maintained in all embodiments of the invention disclosed herein.

The wall thickness of the partitions 48 can be in the range of 10 to 15 mils (0.010 through 0.015) inches).

Approximately eighty percent of the catheter is constituted by the two semi-circular lumen arrangement shown in FIG. 12A. This is a preferred arrangement because there is less blocking of a lumen when the catheter has to bend.

FIG. 13 shows an alternate embodiment of this invention in which the cross-section at A—A of FIG. 11 illustrates shaped lumens 11 and 12 that are substantially equal in a cross-sectional area. The FIG. 13 lumen design transitions to the coaxial design shown in FIG. 12D at the infusion exit port 26 by way of the intermediate arrangement that is shown in FIG. 12C.

FIG. 14 illustrates a further embodiment in which the coaxial design is maintained throughout the tube 24 from juncture 22 to infusion exit port 26. Thus, the FIG. 14 embodiment requires the use of the FIG. 8 web 32 support arrangement over a short distance at the infusion exit port 26.

In the FIG. 14 arrangement, the FIG. 8 web 32 arrangement is limited to a length of three to five millimeters. The use of these radial webs 36 over greater lengths tends to excessively reduce flow through lumen compression when the catheter goes around bends.

FIG. 15 is a longitudinal section illustrating the manner in which the FIG. 12 semi-circular lumens 11 and 12 arrangement is achieved where the infusion tube 18 and aspirating tube 20 are joined. Specifically, as shown in FIG. 15C, the two lumens 11 and 12 become part of the juncture 22. As shown in FIG. 15B, these two lumens are shaped into the approximately semi-circular modes desired. As shown in FIG. 15A, a wall 24 is provided to define these two lumens 11 and 12. This wall 24 is the outer tube 24.

The juncture 22 for the shaped lumens of FIG. 13 would be in all respects like that of FIG. 15 except for the curvature of the lumens at the cross-sections A—A and B—B.

FIG. 16 is a longitudinal sectional view of the juncture 22, similar to that of FIG. 15, showing the arrangement to provide the FIG. 14 co-axial lumen design.

What we claim is:

1. A hemodialysis catheter comprising:

an aspiration lumen and an infusion lumen, said infusion lumen having an exit port arrangement, said infusion lumen being circumferentially deployed around said aspirating lumen in a zone adjacent to said infusion exit port arrangement, said aspiration lumen terminating distally from the distal end of said infusion lumen, said exit port arrangement providing an emission of fluid from said infusion lumen over substantially a 360 degrees zone to provide a circumferential planar jet of fluid with a substantial radial component, said exit port arrangement providing said planar jet constituting the sole exit ports in said infusion lumen.

2. The catheter of claim 1 wherein: said infusion lumen has an axis and the plane of said zone is substantially perpendicular to said axis of said infusion lumen.

3. The catheter of claim 2 further comprising:

a wall on the catheter at a position adjacent to and distal of said infusion exit port arrangement to assure a substantial radial component for fluid flow from said infusion exit port arrangement.

4. The catheter of claim 2 wherein:

said exit port arrangement in said zone are first and second sets of arcuate ports along first and second adjacent and parallel planes respectively, each port in one of said planes partially circumferentially overlapping adjacent ports in the other one of said planes.

5. The catheter of claim 2 wherein: said exit port arrangement in said zone is a set of elongate ports at an angle to said plane, each of said ports partially circumferentially overlapping adjacent ones of said ports.

6. The catheter of claim 1 further comprising:

a wall on the catheter at a position adjacent to and distal of said infusion exit port arrangement to assure a substantial radial component for fluid flow from said infusion exit port arrangement.

7. The catheter of claim 6 wherein:

said exit port arrangement in said zone comprises: a set of openings at the distal end of said infusion lumen, said openings extending to said circumferential wall, and a set of separator webs between said openings.

8. The method of blood treatment employing a hemodialysis catheter having an aspiration lumen with an aspiration port and an infusion lumen having an infusion port arrangement to provide filtered blood comprising the steps of:

positioning the infusion port proximally of the aspiration port, and infusing treated blood into the patient as a planar jet having a substantial radial component extending substantially 360 degrees in a zone around the periphery of the catheter, and providing infusion ports solely in said zone.

9. The method of claim 8 further comprising the step of: eroding occlusion buildup at the site of said infusing.

10. In the method of aspirating blood through an aspirating port of a hemodialysis catheter, filtering the blood and infusing the filtered blood back into a patient through an infusion port arrangement of the catheter, the improvement comprising the steps of:

infusing the filtered blood in a planar jet along a zone substantially 360 degrees around the periphery of the catheter, providing infusion ports solely in said zone, providing the aspiration port at a position distal of said infusion port arrangement, and at the infusion port arrangement, eroding occlusive material that grows along the outer surface of the catheter.

* * * * *